(12) United States Patent
Deren

(10) Patent No.: US 10,660,782 B2
(45) Date of Patent: May 26, 2020

(54) INFLATABLE SPLINT FOR MEDICAL TREATMENT

(71) Applicant: Jeffrey A. Deren, Winter Park, FL (US)

(72) Inventor: Jeffrey A. Deren, Winter Park, FL (US)

(*) Notice: Subject to any disclaimer, the term of this patent is extended or adjusted under 35 U.S.C. 154(b) by 385 days.

(21) Appl. No.: 15/637,794

(22) Filed: Jun. 29, 2017

(65) Prior Publication Data

US 2018/0000626 A1 Jan. 4, 2018

Related U.S. Application Data

(60) Provisional application No. 62/356,664, filed on Jun. 30, 2016.

(51) Int. Cl.
*A61F 5/058* (2006.01)

(52) U.S. Cl.
CPC ...... *A61F 5/05816* (2013.01); *A61F 5/05858* (2013.01); *A61F 5/05866* (2013.01)

(58) Field of Classification Search
CPC .... A61F 5/012; A61F 5/05816; A61F 5/0111; A61F 5/0102; A61F 5/0127; A61F 2007/0032; A61F 5/0118; A61F 5/013; A61F 5/05841; A61F 5/32; A61F 2007/0091; A61F 13/064; A61F 2007/003; A61F 2007/0039; A61F 5/3723; A61F 5/3761; A61F 5/05866; A61F 5/05875; A61F 2007/0035; A61F 2007/0036; A61F 5/05858; A61F 13/104; A61F 2007/0037; A61F 2007/0045; A61F 2007/023; A61F 2/586; A61F 5/0106; A61F 5/0123; A61H 2201/1697; A61H 2205/12; A61H 2201/1635; A61H 2201/164; A61H 1/024; A61H 1/0266; A61H 1/0274; A61H 1/0277; A61H 1/0285; A61H 1/0288; A61H 2201/0103
USPC ......................................... 602/13, 20–22, 30
See application file for complete search history.

(56) References Cited

U.S. PATENT DOCUMENTS

| 4,281,647 A | 8/1981 | Antypas |
| 5,152,740 A | 10/1992 | Harkensee et al. |
| 5,427,577 A * | 6/1995 | Picchietti ............... A61F 5/0118 2/161.1 |

(Continued)

OTHER PUBLICATIONS

PCT International Searching Authority: International Search Report and Written Opinion dated Sep. 14, 2017; entire document.

*Primary Examiner* — Ophelia A Hawthorne
(74) *Attorney, Agent, or Firm* — Reichel Stohry Dean LLP; Mark C. Reichel; Natalie J. Dean

(57) ABSTRACT

An inflatable splint can include a sleeve shaped to conform to a specific human body part and a plurality of inflatable chambers disposed on the sleeve. The sleeve, in cooperation with the plurality of chambers in an inflated condition, can be contoured to maintain the specific human body part in a desired position. A method of using an inflatable splint includes admitting a body part into a sleeve of the inflatable splint and positioning the sleeve around the body part One or more of the plurality of air chambers are selectively inflated such that the flexible sleeve in cooperation with the plurality of chambers in inflated condition is contoured and positioned to maintain the specific human body part in a desired position.

28 Claims, 22 Drawing Sheets

(56) References Cited

U.S. PATENT DOCUMENTS

| | | | | |
|---|---|---|---|---|
| 6,000,059 | A | * 12/1999 | Abts | A41D 19/015 2/161.6 |
| 6,146,347 | A | 11/2000 | Porrata | |
| 6,719,711 | B1 | * 4/2004 | Islava | A61F 5/05816 128/DIG. 20 |
| 2002/0116743 | A1 | 8/2002 | Tourbier et al. | |
| 2008/0058911 | A1 | 3/2008 | Parish et al. | |
| 2011/0201981 | A1 | 8/2011 | Deshpande et al. | |
| 2013/0053739 | A1 | * 2/2013 | Mustafa | A61F 5/05816 602/13 |
| 2016/0081843 | A1 | * 3/2016 | Eriksson | A61F 5/0118 602/6 |

* cited by examiner

INFLATABLE SPLINT FOR MEDICAL TREATMENT

CROSS-REFERENCE TO RELATED APPLICATIONS

The present application claims the benefit of U.S. Provisional Patent Application Ser. No. 62/356,664, filed on Jun. 30, 2016, the contents of which are herein incorporated by reference in their entirety.

FIELD OF THE INVENTION

The present invention relates to inflatable splints, and more particularly, to an inflatable splint for medical treatment.

BACKGROUND OF THE INVENTION

Paramedics and other emergency response personnel often utilize emergency immobilization splints for arms and legs for patient transport. Such devices cannot, however, maintain an extremity in a particular position, especially a hand. Splints made of plaster and fiberglass can be used for this purpose, but they must be applied by trained medical personnel. In practice, however, such splints are often applied inappropriately, the limb is not positioned well or the splint is too tight, etc.—potentially worsening a patient's condition before the patient can be seen a specialist. Other disadvantages of current splints include overall bulkiness and cumbersomeness when applying the splint to a limb. After the splint has been inflated, a patient is usually unable adjust the splint appropriately. The cost of manufacture for current splints is comparatively high. Further advances in medical splint technology are possible.

SUMMARY OF THE INVENTION

In view of the foregoing, it is an object of the present invention to provide an inflatable splint for medical treatment. According to one embodiment of the present invention, the inflatable splint can include a sleeve shaped to conform to a specific human body part and a plurality of Inflatable chambers disposed on the sleeve. The sleeve, in cooperation with the plurality of chambers in an inflated condition, can be contoured to maintain the specific human body part in a desired position.

According to another embodiment of the present invention, a method of using an inflatable splint includes admitting a body part into a sleeve of the inflatable splint and positioning the sleeve around the body part. One or more of the plurality of air chambers are selectively inflated such that the flexible sleeve in cooperation with the plurality of chambers in inflated condition is contoured and positioned to maintain the specific human body part in a desired position.

According to another embodiment of the present invention, a method of making an inflatable splint includes determining locations of a plurality of air chambers on a sheet and positioning respective molds of predetermined dimension on the determined locations of the plurality of air chambers. The plurality of air chambers are formed on the sheet based on the respective molds at the determined locations. One or more loops and fasteners are attached on at least one longitude edge of the sheet.

These and other objects, aspects and advantages of the present invention will be better appreciated in view of the drawings and following detailed description of preferred embodiments.

DETAILED DESCRIPTION OF PREFERRED EMBODIMENTS

According to one embodiment of the present invention, an inflatable splint is used for limb immobilization or traction. The inflatable splint includes a sleeve portion shaped to conform to a specific human body part (e.g., a hand, a foot, a leg, an arm, a joint, etc.) and a plurality of tubular chambers contoured and positioned to provide optimum support for certain area of the specific body part. With reference to FIGS. 1-23, the assembly of the structural elements and further features thereof will be described here. These structural elements are selected for exemplary and illustrative purposes, and it will be appreciated the present invention is not necessarily limited thereto.

Figure 1:
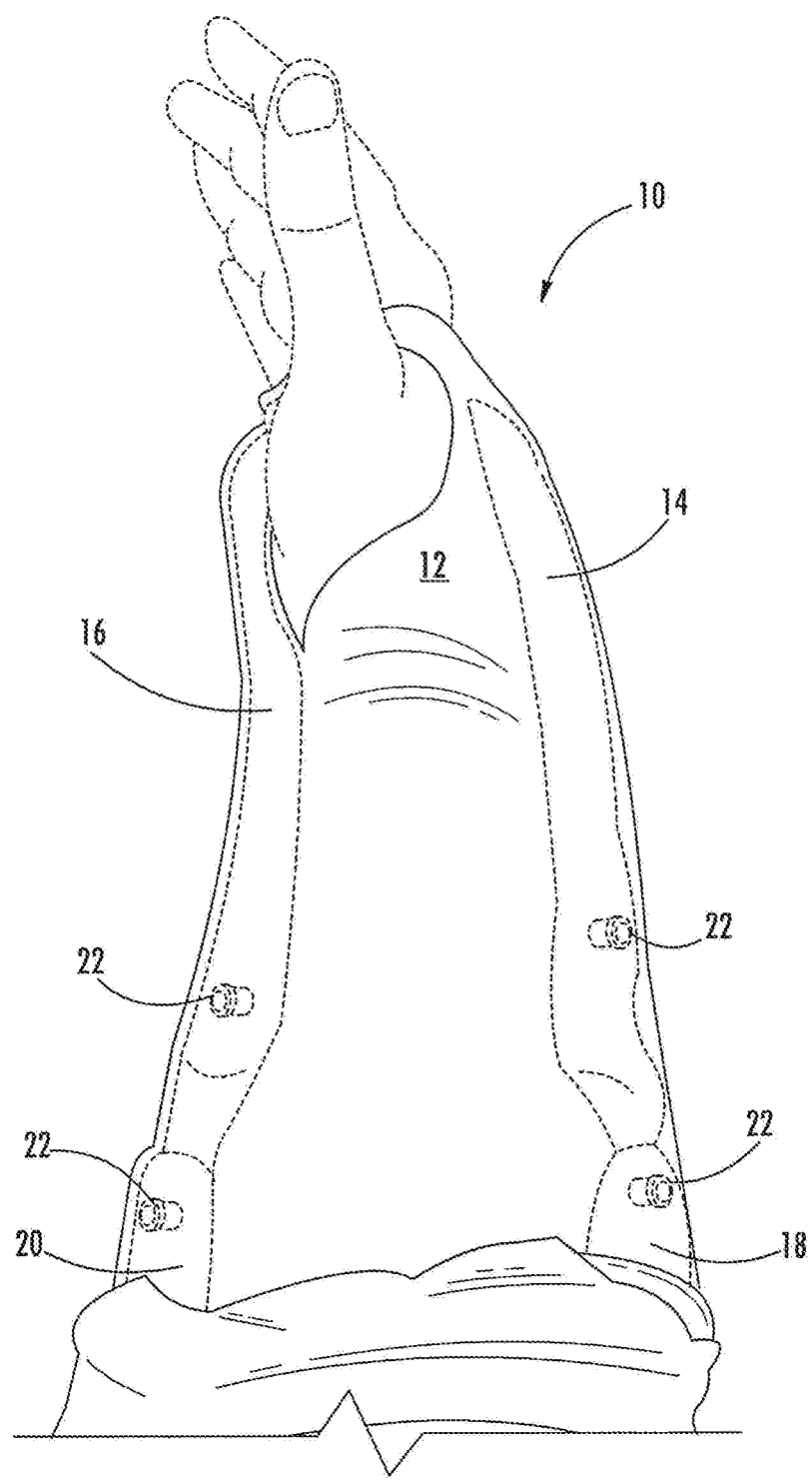
FIG. 1 is a perspective view of dorsal side and ventral side of a forearm and a hand applied with an inflatable splint, according to one embodiment of the present invention.
Figure 2:
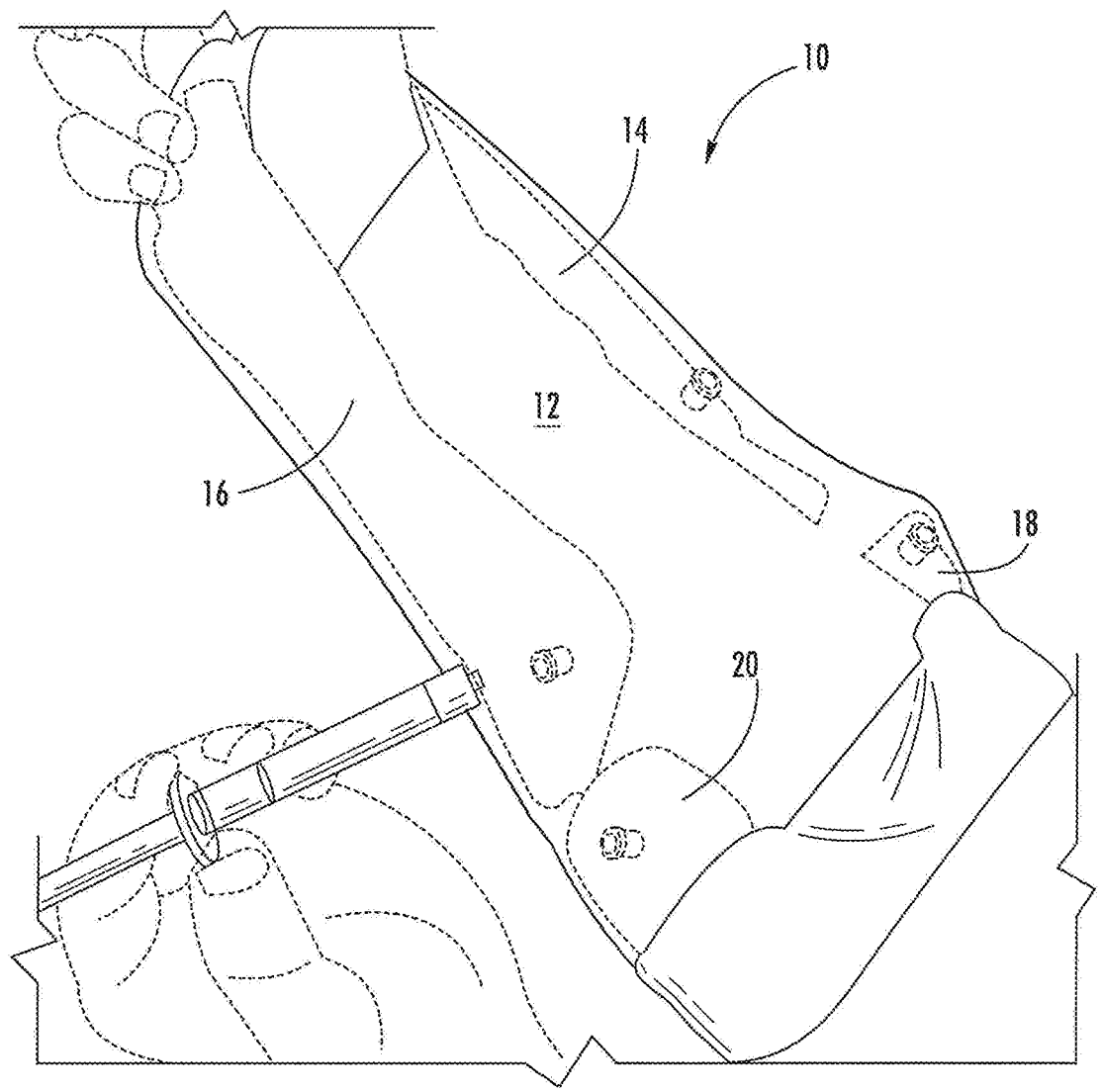
FIG. 2 is perspective view of the ventral side of a forearm and a hand applied with the inflatable splint of FIG. 1.

In one embodiment, referring to FIGS. 1-2, an exemplary inflatable splint 10 can be used for an arm and/or a hand of a patient. The inflatable splint 10 includes a sleeve 12 shaped to conform a forearm and four separately inflatable lengthwise tubular chambers 14, 16, 18 and 20. A patient's forearm is admitted into the sleeve 12, which is then secured to the palm between the thumb and the index finger. In the depicted embodiment, the first chamber 14 surrounds a portion of the dorsal side of the hand and the lower forearm, the second chamber 16 surrounds a portion of the palmar side of the hand and the lower forearm, the third chamber 18 surrounds the dorsal side of the upper forearm, and the fourth chamber 20 surrounds the palmar side of the upper forearm. The plurality of conjoined air chambers 14, 16, 18 and 20 can surround at least a portion of the radius and the ulna bones in the forearm and/or at least a portion of dorsal side or palmar side of the hand to provide a desired position and/or orientation for the forearm and/or hand.

Each of the plurality of chambers 14, 16, 18 and 20 can be inflated independently via a port with a suitable valve 22 for introducing air into the respective chambers. Adjacent chamber cells can also be connected for air flow communication at their ends by restricted passageways. An advantage of valve 22 is a stem to enable the air chambers to be inflated by mouth, a pump, a syringe, or other mechanical means. Any of various valve constructions known to the art can be used. The degree of compression can be controlled by the pressure to which the bandage splint is inflated.

The air chambers in any particular case can have different shapes and sizes, depending on the type of injury and the specific body part to be immobilized. In the depicted embodiments, the air chambers are generally rectangular in shape with rounded corners. The air chambers are shaped and arranged such that the body part is immobilized at its neutral position and/or held at the desired angle and/or orientation in relation to other body parts. Right limbs could require different splints from left limbs.

Figure 3:
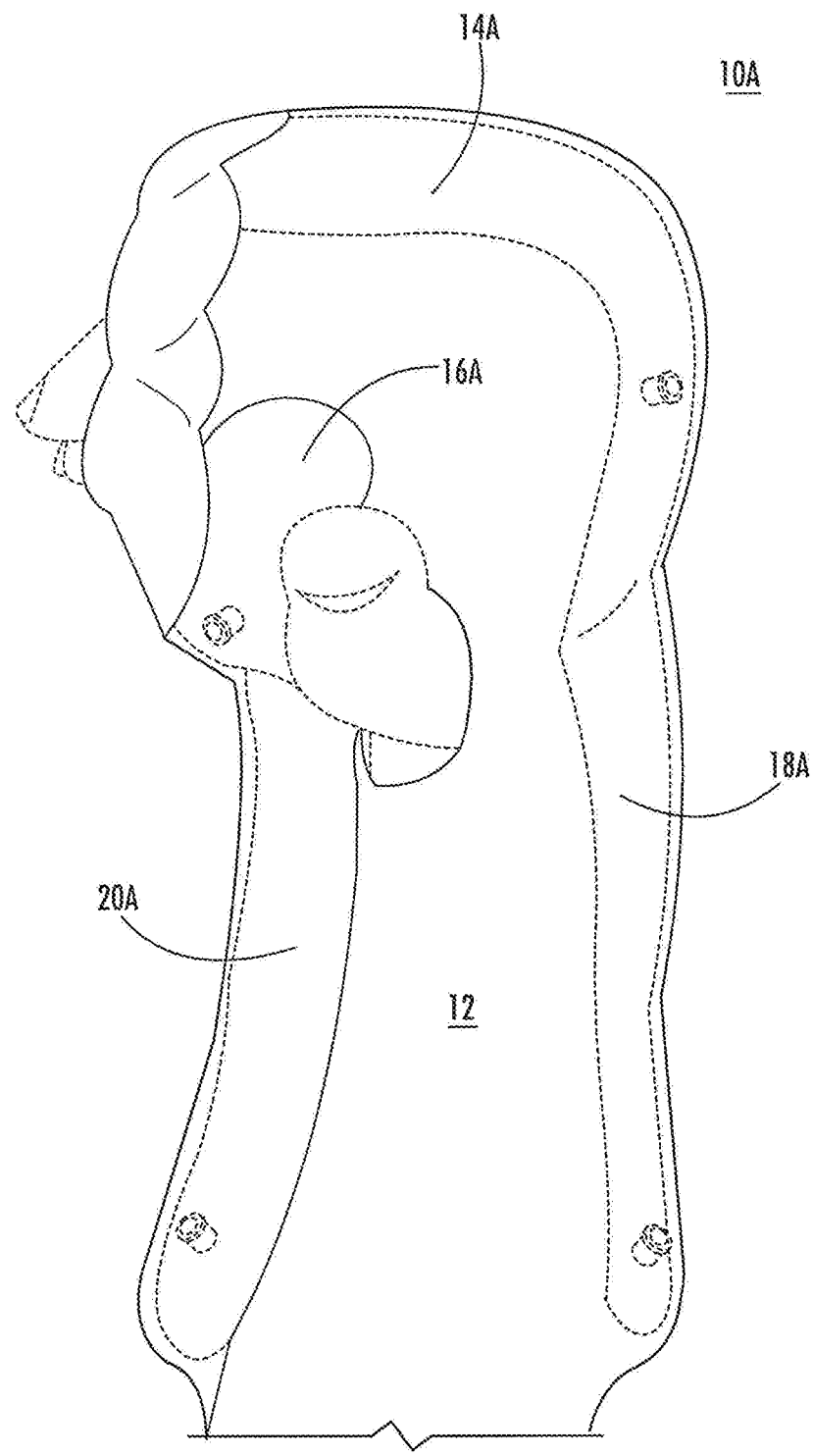
FIG. 3 is a perspective view of dorsal side and ventral side of a forearm and a hand applied with an inflatable splint, according to another embodiment of the present invention.
Figure 4:
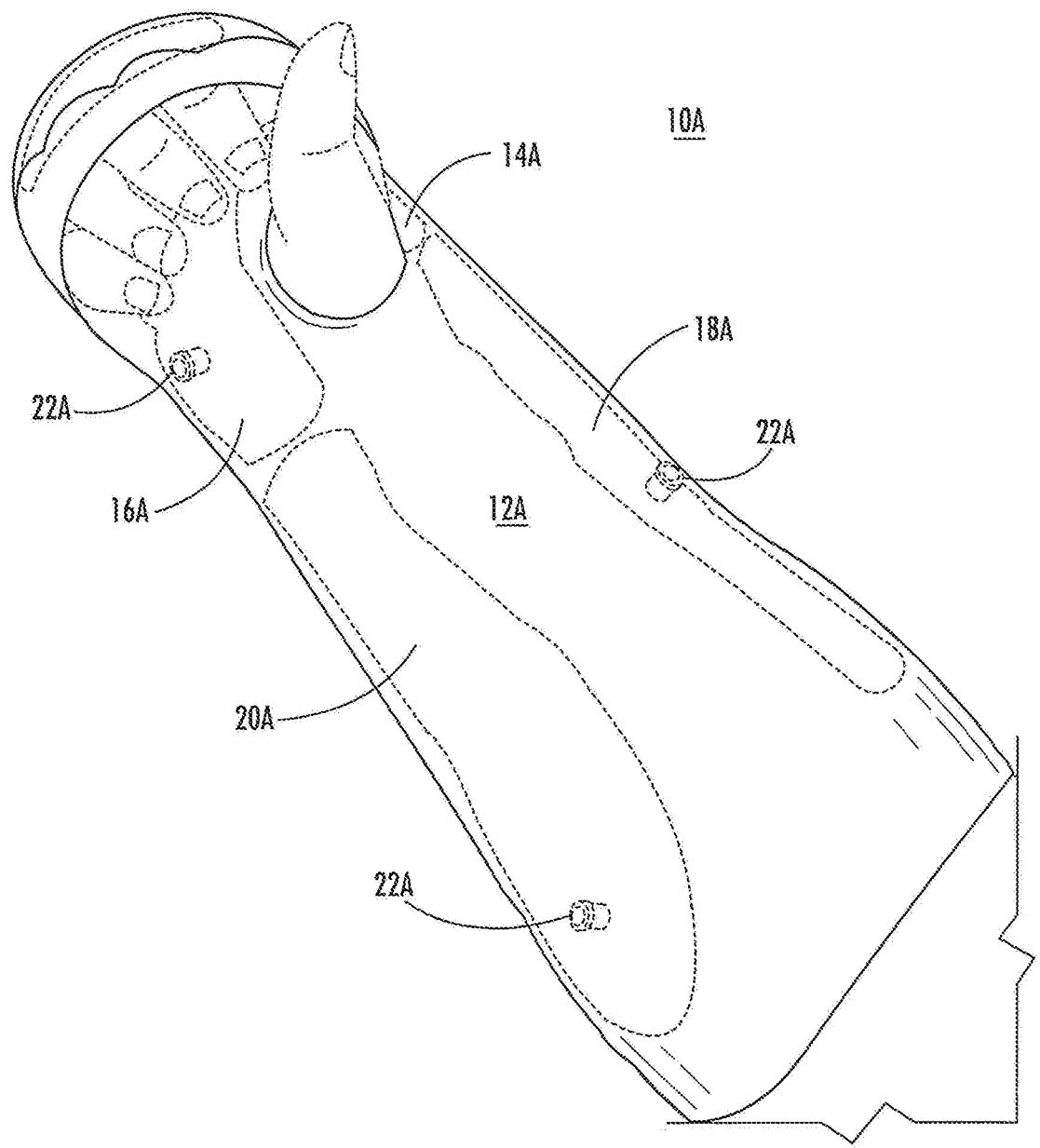
FIG. 4 is a perspective view of the ventral side of a forearm and a hand applied with the inflatable splint of FIG. 3.

In another embodiment, referring to FIGS. 3-4, an inflatable splint 10A adapted for immobilizing a patient's hand and forearm includes a sleeve 12A and four lengthwise-extending tubular chambers: a first chamber 14A surrounding a portion of the dorsal side of a hand, a second chamber 16A surrounding a portion of the palmar side of the hand, a third chamber 18A surrounding the dorsal side of a forearm, and a fourth chamber 20A surrounding the palmar side of the forearm. The chambers 14 and 16 are conjoined and adapted to fit to the upper arm and in the palm of a patient's hand between the thumb and fingers. Additional straps, such as Velcro straps or other connecting methods, can be used for further securing the splint 10A to its intended position and/or orientation. The additional straps can be further adjusted to fit the dimension of a limb and/or joint.

Figure 5:
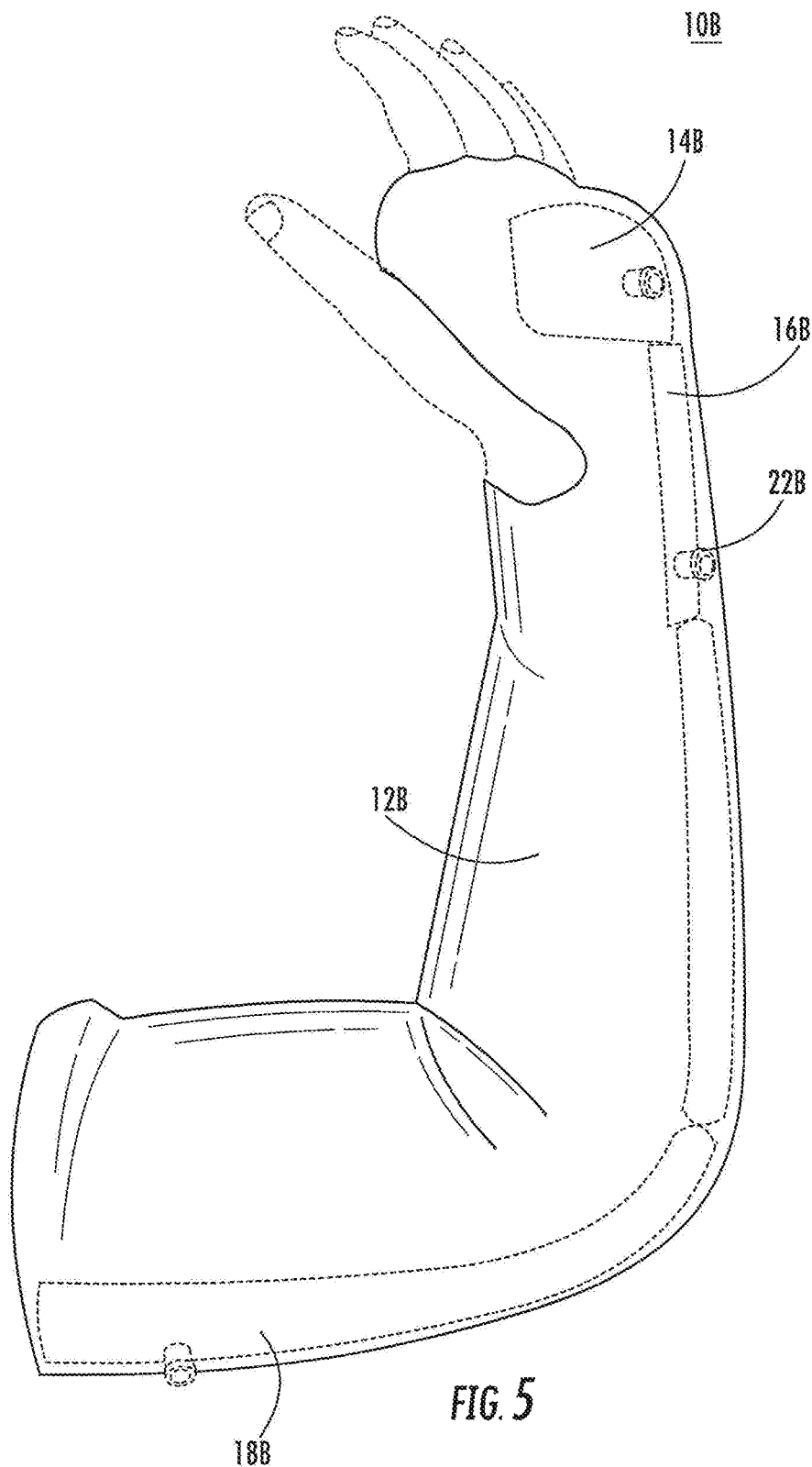
FIG. 5 is a perspective view of dorsal side of a forearm and a hand applied with an inflatable splint, according to yet another embodiment of the present invention.
Figure 6:
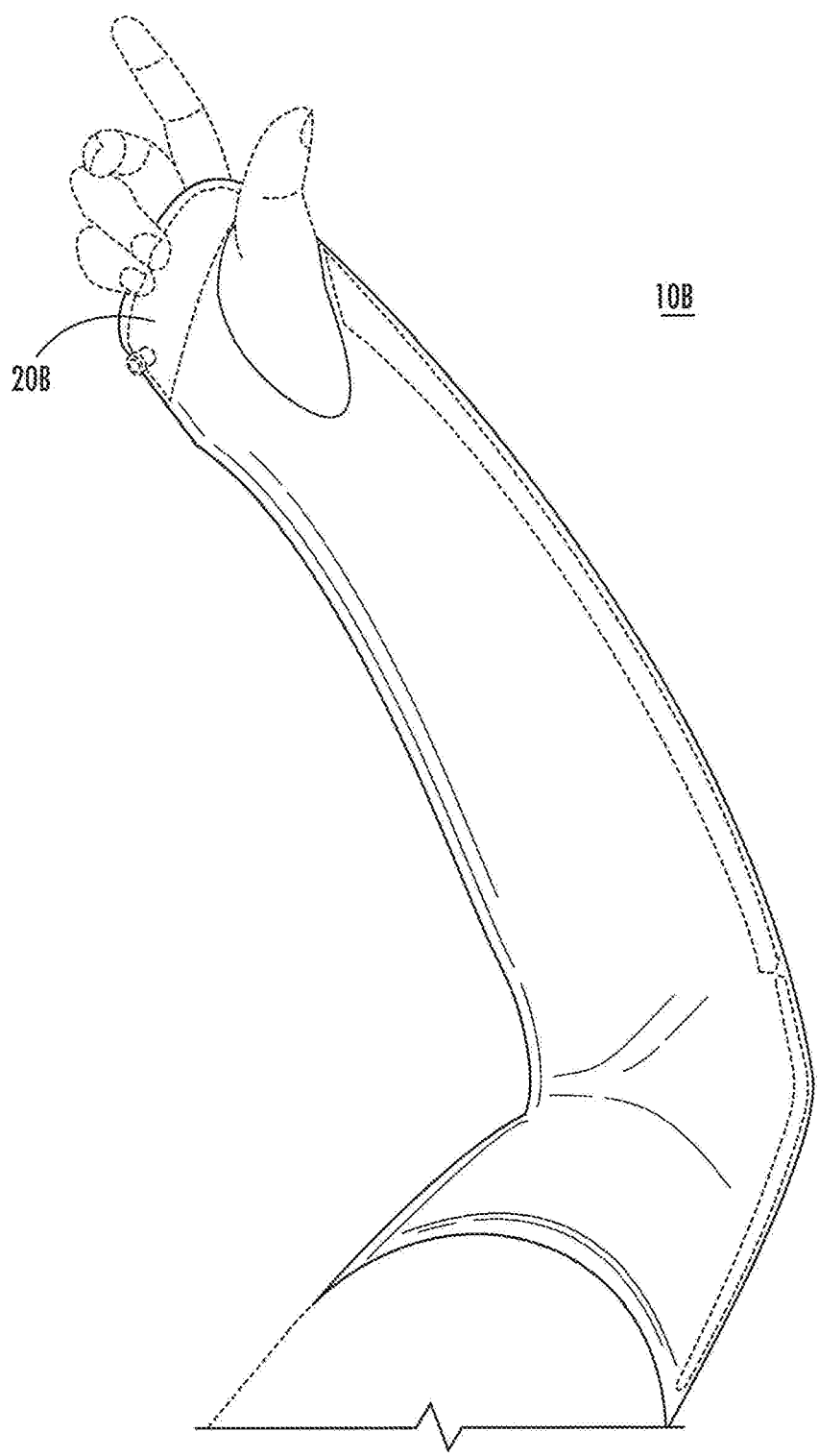
FIG. 6 is a perspective view of the ventral side of a forearm and a land applied with the inflatable splint of FIG. 5.

In yet another embodiment, referring to FIGS. 5-6, an inflatable splint 10B used for a patient's hand, wrist, forearm and/or elbow includes a sleeve 12B and four lengthwise-extending tubular chambers; a first chamber 14B surrounding a portion of the dorsal side of a hand, a second chamber 16B surrounding the dorsal side of a lower arm, a third chamber 18B surrounding the dorsal side of an upper arm, and a fourth chamber 20B surrounding the palmar side of the hand.

Figure 7:
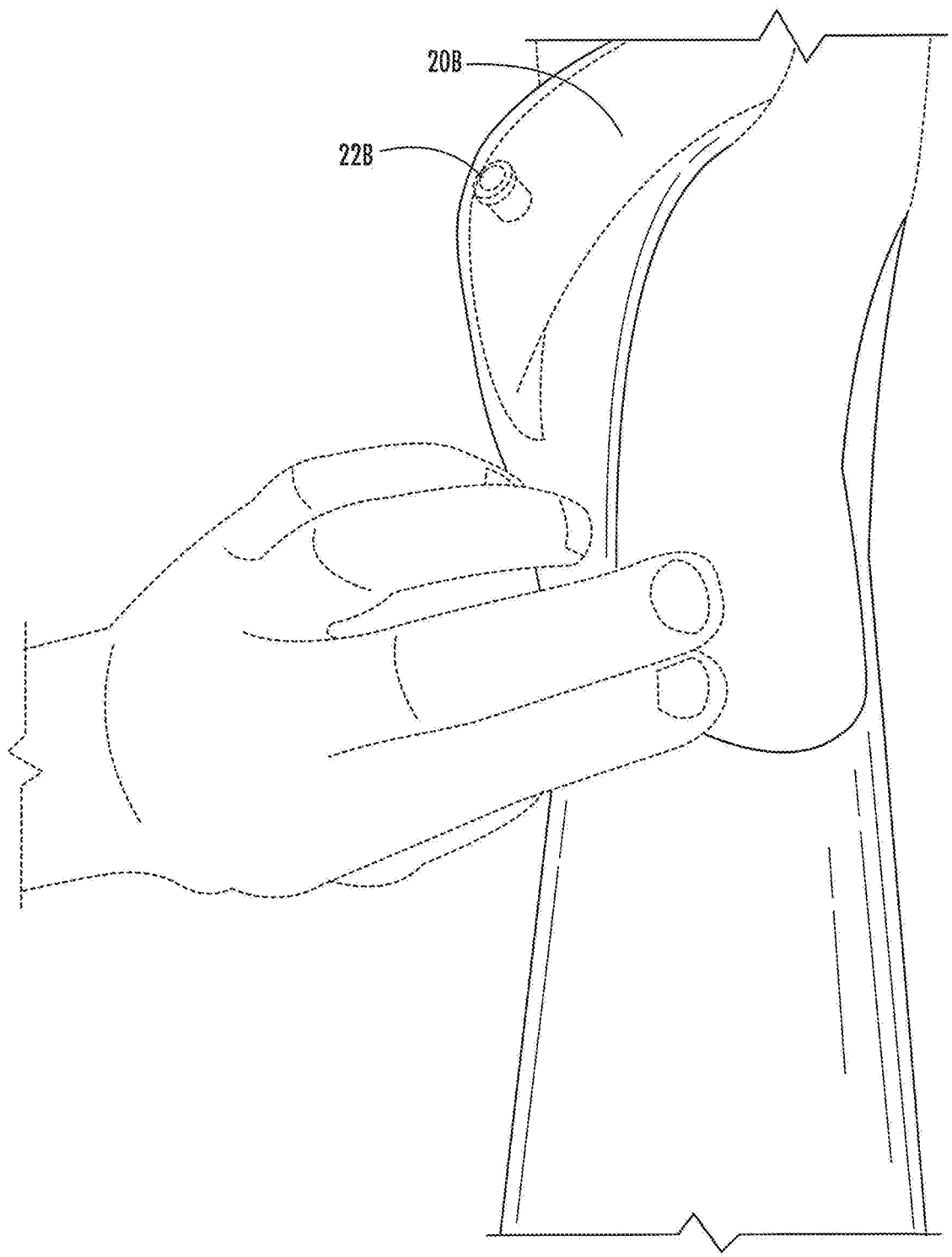
FIG. 7 is a perspective view of the ventral side of a forearm applied with an inflatable splint, leaving the pulse checking area accessible, according to another embodiment of the present invention.
Figure 8:
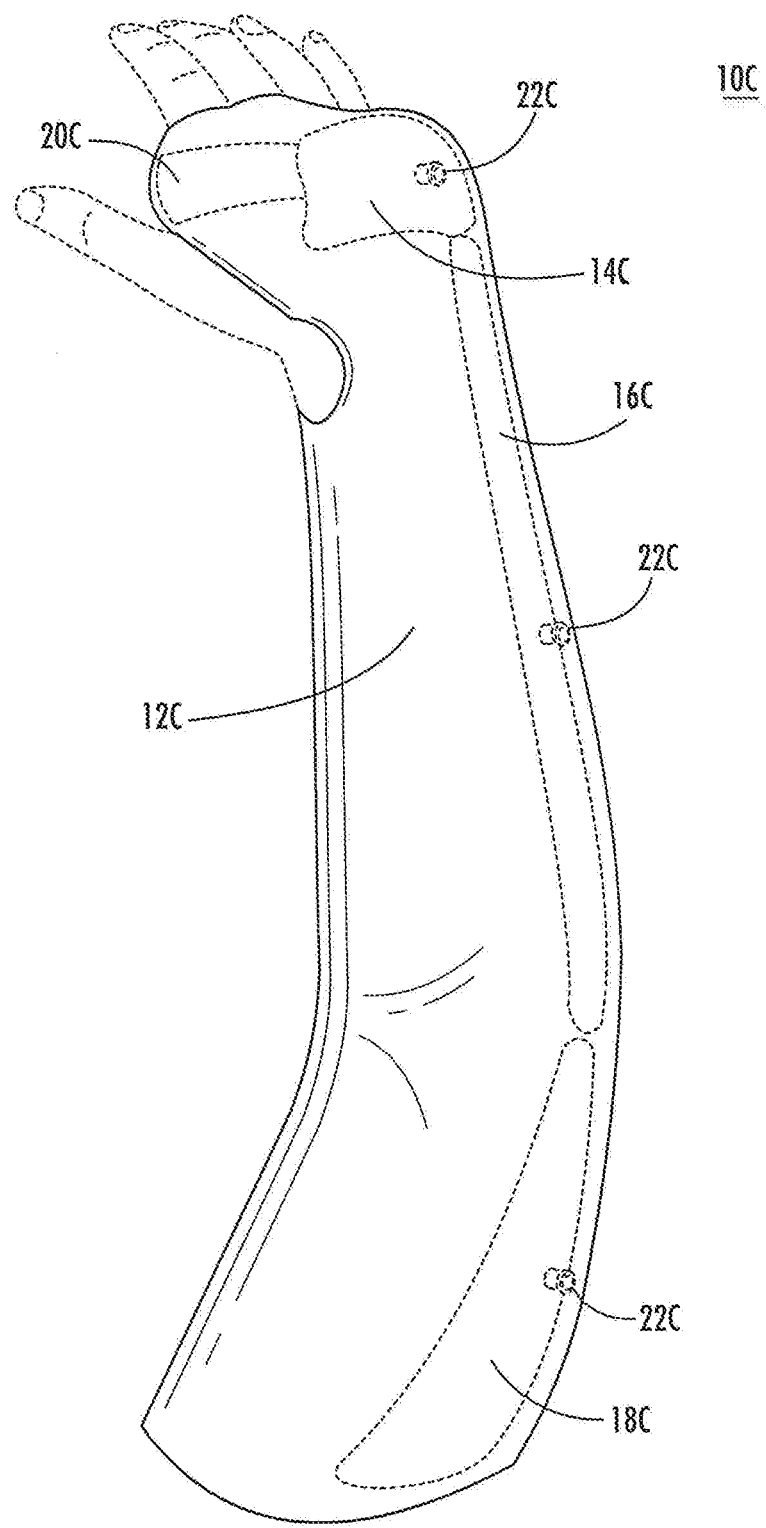
FIG. 8 is a perspective view of dorsal side of a forearm and a hand applied with an inflatable splint, according to yet another embodiment of the present invention.
Figure 9:
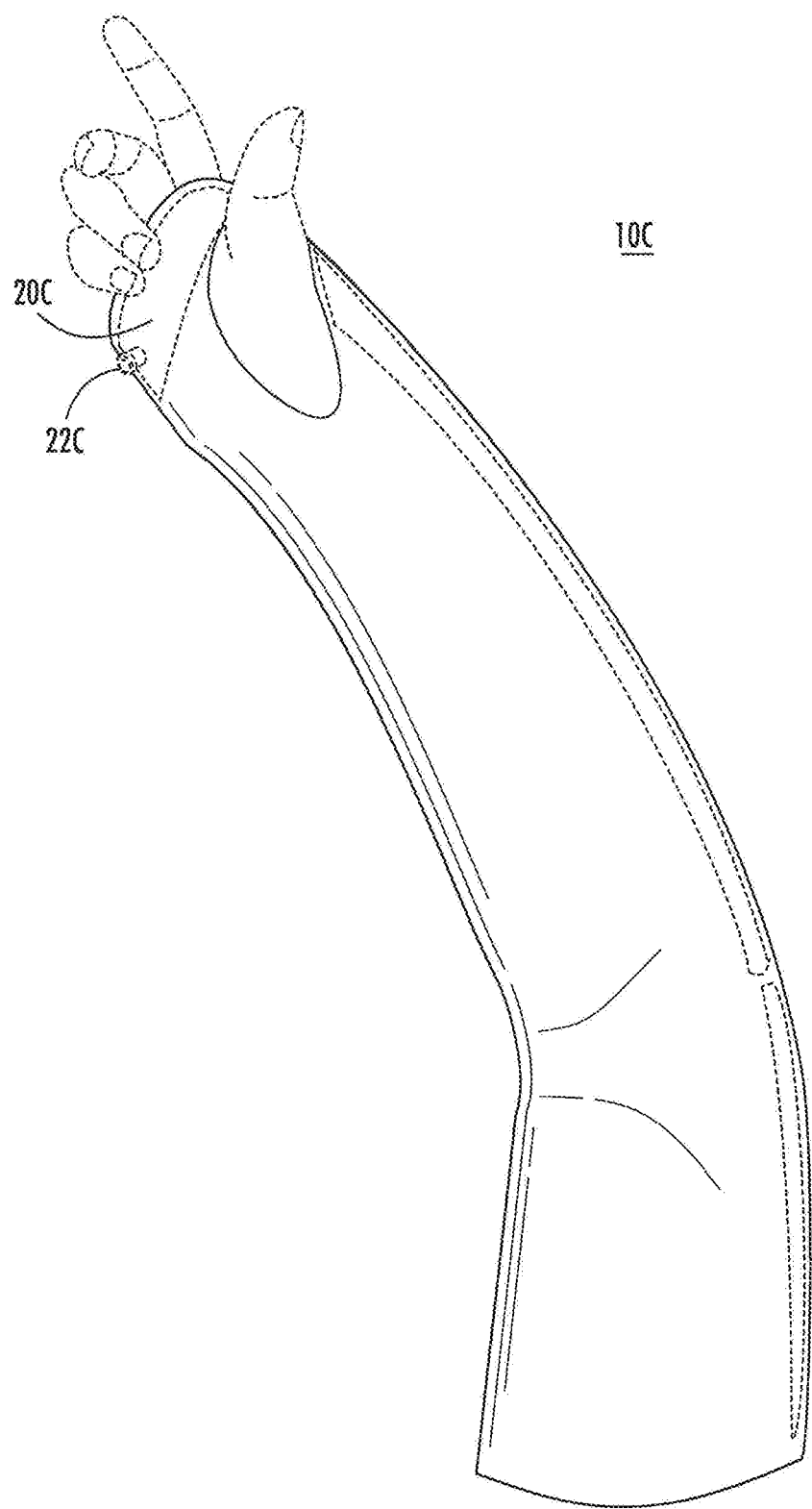
FIG. 9 is a perspective view of the ventral side of a forearm and a hand applied with the inflatable splint of FIG. 8.

In yet another embodiment, referring to FIGS. 7-9, an inflatable splint 10C for a patient's hand and/or forearm includes a sleeve 12C and four separately inflatable chambers: a first chamber 14C surrounding a portion of the dorsal side of a hand, a second chamber 16C surrounding the dorsal side of a lower arm, a third chamber 18C surrounding the dorsal side of an upper arm, and a fourth chamber 20C surrounding the palmar side of the hand.

The embodiment shown in FIGS. 5-6 and 7-9 are the same, excepting the contour and position of a plurality of inflated air chambers which together define a different position and/or orientation for the elbow. More specifically, FIGS. 5-6 show an inflatable splint 10B holding an elbow at an approximately right angle, and FIGS. 7-8 show an inflatable splint 10C holding an elbow at a more extended angle.

The plurality of lengthwise-extending tubular chambers in splint 10A, 10B and 10C can be positioned and/or orientated such that an arm pulse checking point is accessible, as shown in FIG. 7.

Figure 10:
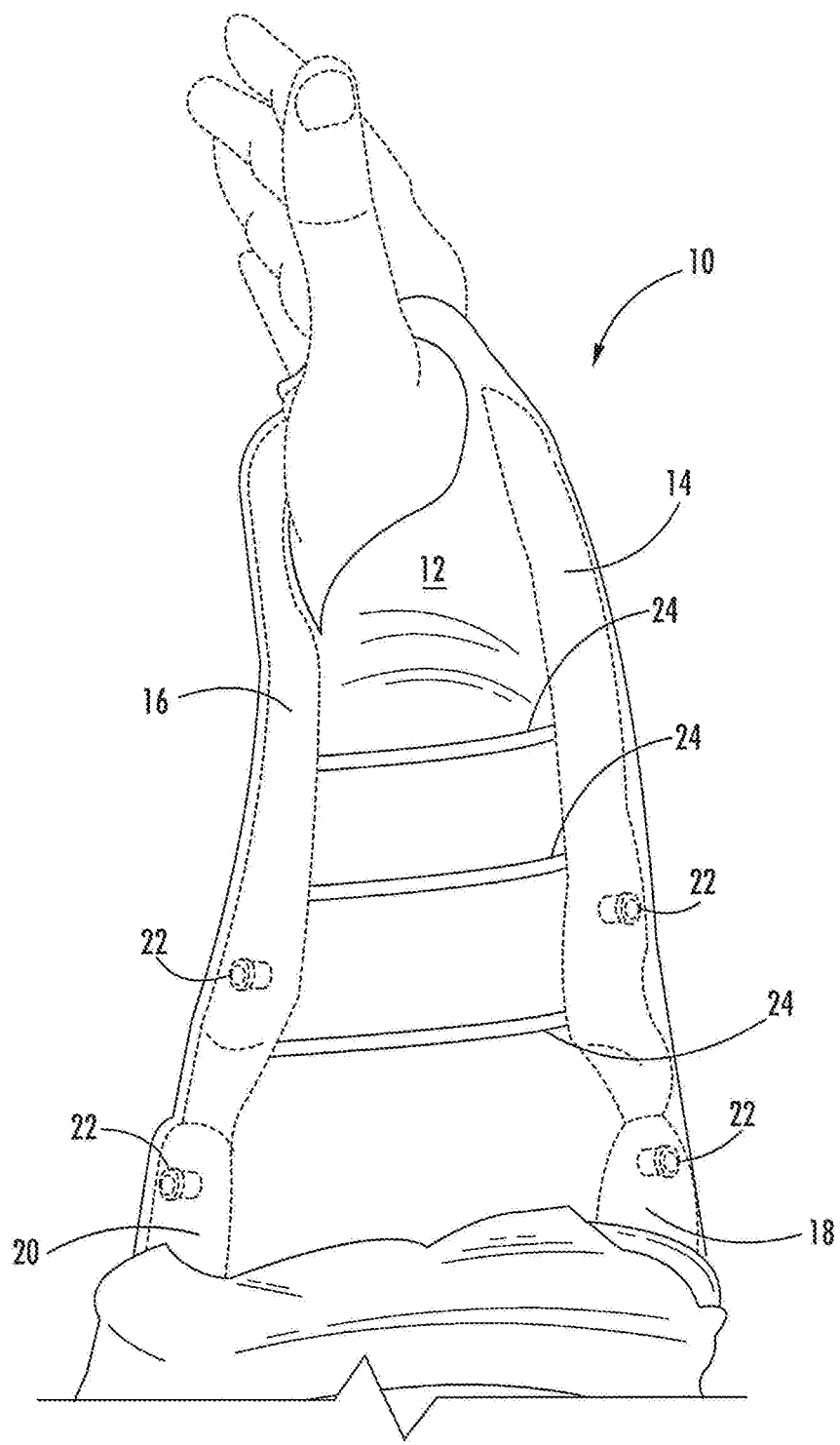
FIG. 10 is a perspective side view of the inflatable splint of FIG. 1 with extra straps to secure the splint in place.

The additional straps 24 can be further adjusted to fit the dimension of a limb and/or joint. Referring to FIG. 10, a plurality of annular straps 24 connecting air chambers can be connected to the suitable portions of the air chambers to secure the splint 10 in the desired position and/or orientation.

Figure 11:
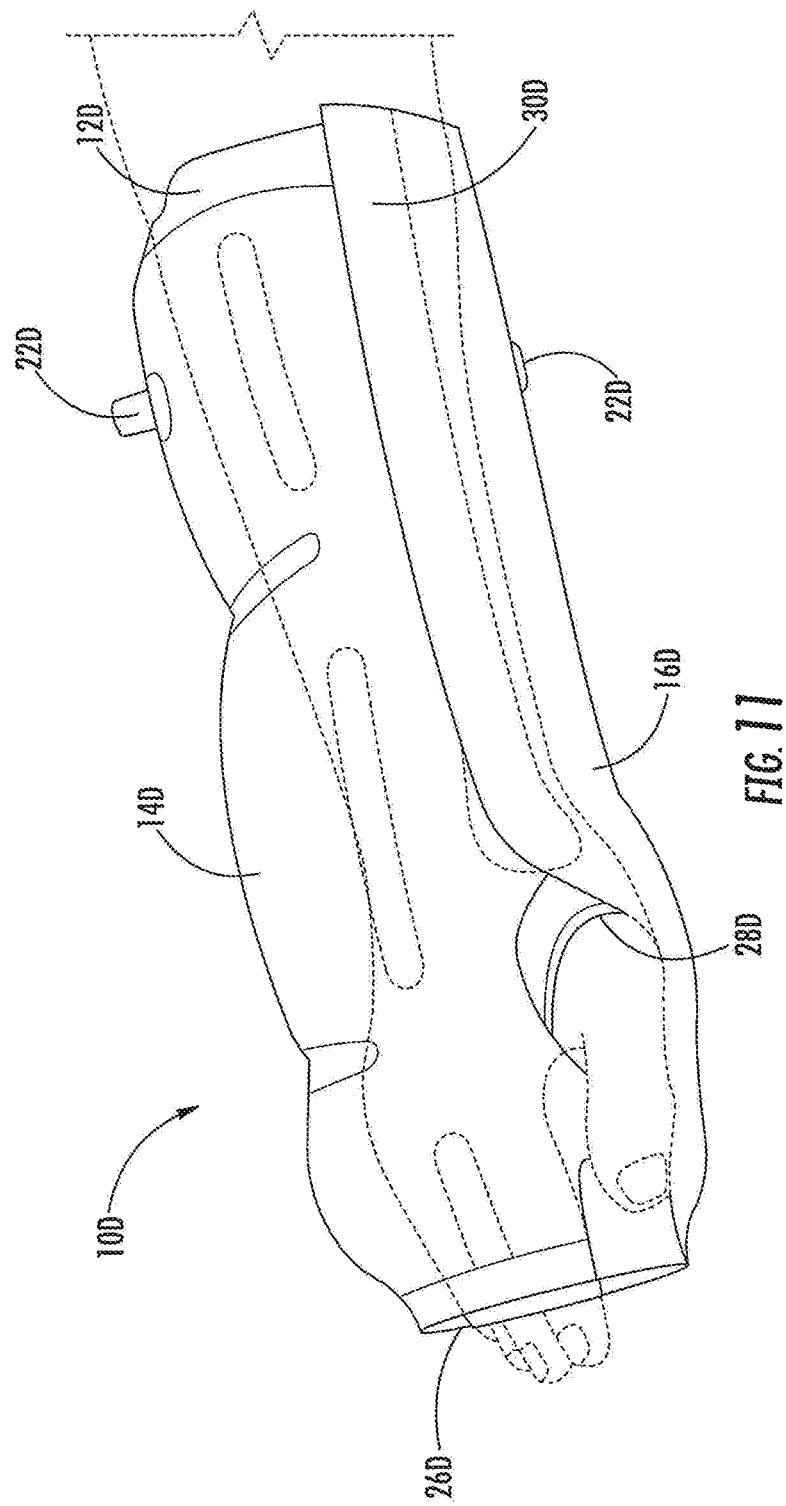
FIG. 11 is a perspective side view of an inflatable splint applied to a hand and a forearm, according to another embodiment of the present invention.

Referring to FIG. 11, a splint 10D includes a sleeve 12D shaped to conform to a portion of a hand and a lower arm. A plurality of chambers includes a chamber 14D surrounding at least a portion of a dorsal side of the hand and a dorsal side of the lower arm, a chamber 16D surrounding at least a portion of a palmar side of the hand and a palmar side of the lower arm. The splint 10D has an open lower end 26D to expose four fingers and allow airflow into the splint 10D. The splint 10D also has an opening 28D for a thumb to pass through. The chamber 14D and the chamber 16D each includes a valve 22D for introducing air into the respective chamber. In the depicted embodiment, the sleeve 12D is formed from a sheet that has hooks and fasteners 30D attached along the longitudinal edge of the sheet to wrap the sheet into a tubular configuration. Example hooks and fasteners include Velcro fasteners or other suitable fasteners. Velcro fasteners can be welded by applying radio frequency (RF) radiation or sewn to the sheet.

Figure 12:
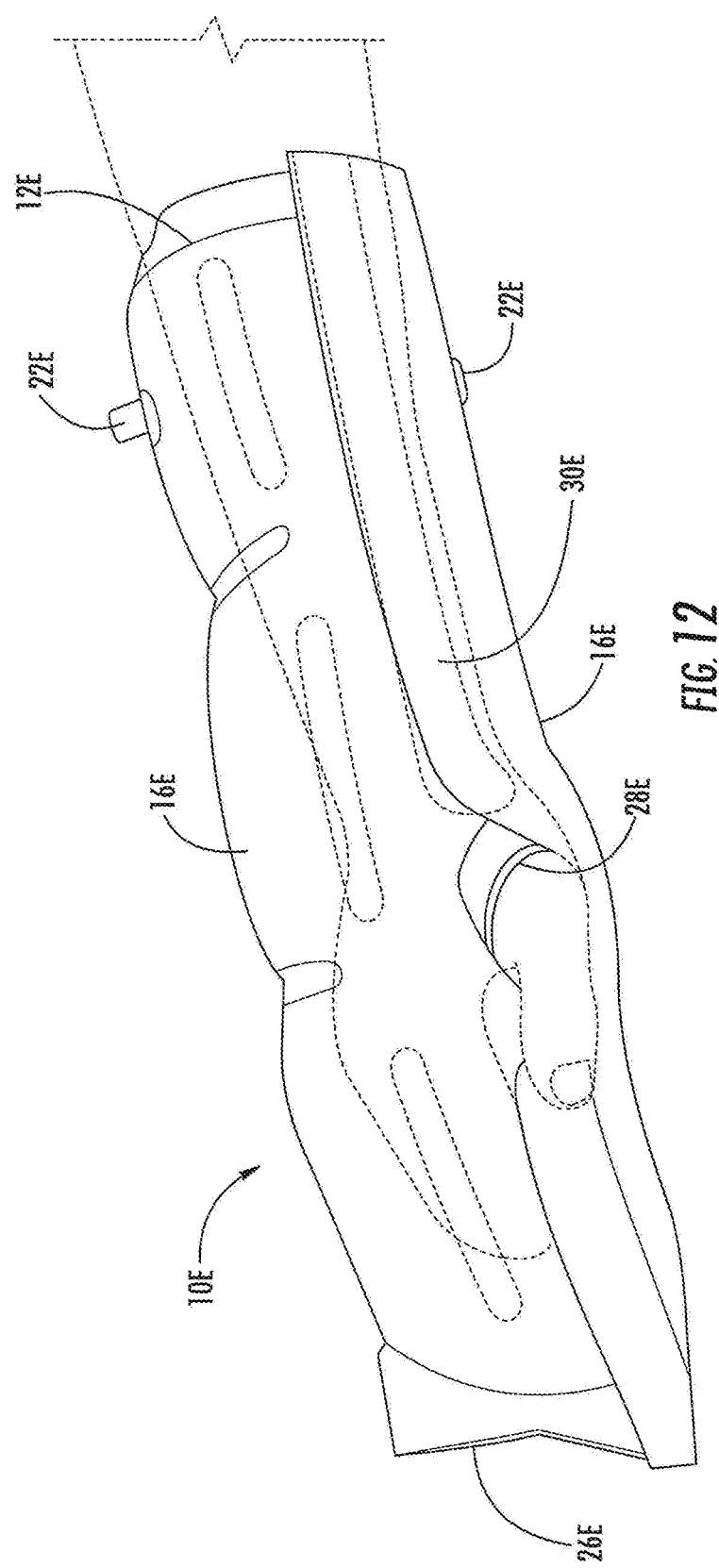
FIG. 12 is a perspective side view of an inflatable splint applied to a hand and a forearm, according to another embodiment of the present invention.

Referring to FIG. 12, according to another embodiment of the present invention, splint 10E is similar to splint 10D except that splint 10E has a closed lower end 26E rather than an opening 26D to expose four fingers.

Figure 13:
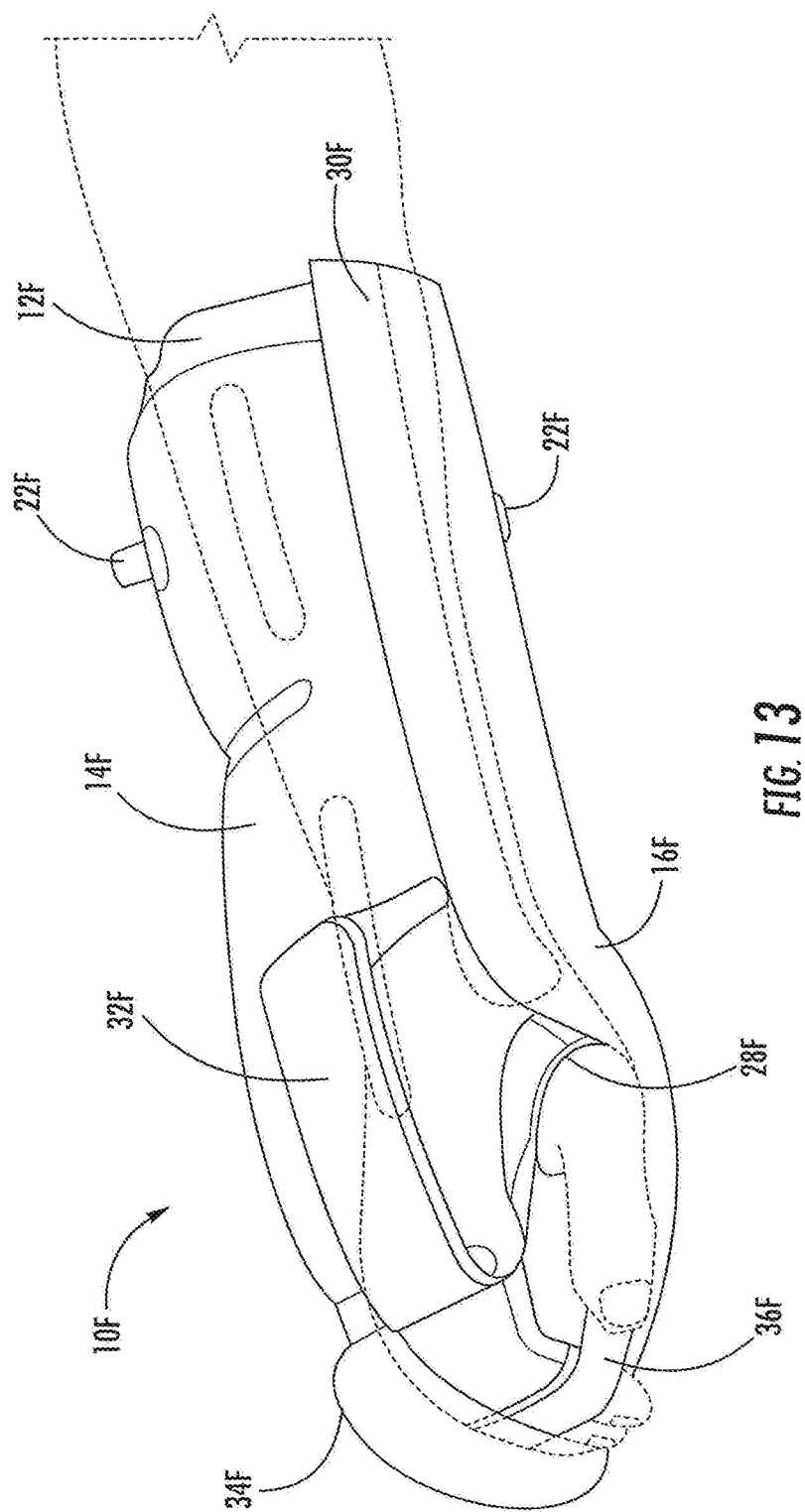
FIG. 13 is a perspective side view of an inflatable splint applied to a hand and a forearm, according to another embodiment of the present invention.

Referring to FIG. 13, according to another embodiment of the present invention, the splint 10F includes four chambers: a chamber 14F surrounding a portion of a dorsal side of the hand and the portion of the arm, a chamber 16F surrounding a portion of a palmar side of the hand and a portion of the arm, a chamber 32F surrounding dorsal side of index finger and middle finger, and a chamber 34F surrounding dorsal side of ring finger and little finger. The chambers 32F and 34F are separately inflatable. In the depicted embodiment of FIG. 13, the chamber 34F can be inflated to hold the ring finger and the little finger in a desired position (e.g., half curled position). The chamber 32F can also be deflated and strapped backwards to keep the corresponding fingers outside the splint 10F. The splint 10F can also have at least one finger strap 36F to hold specific fingers (e.g., the index finger and middle finger) in a bent position.

Figure 14:
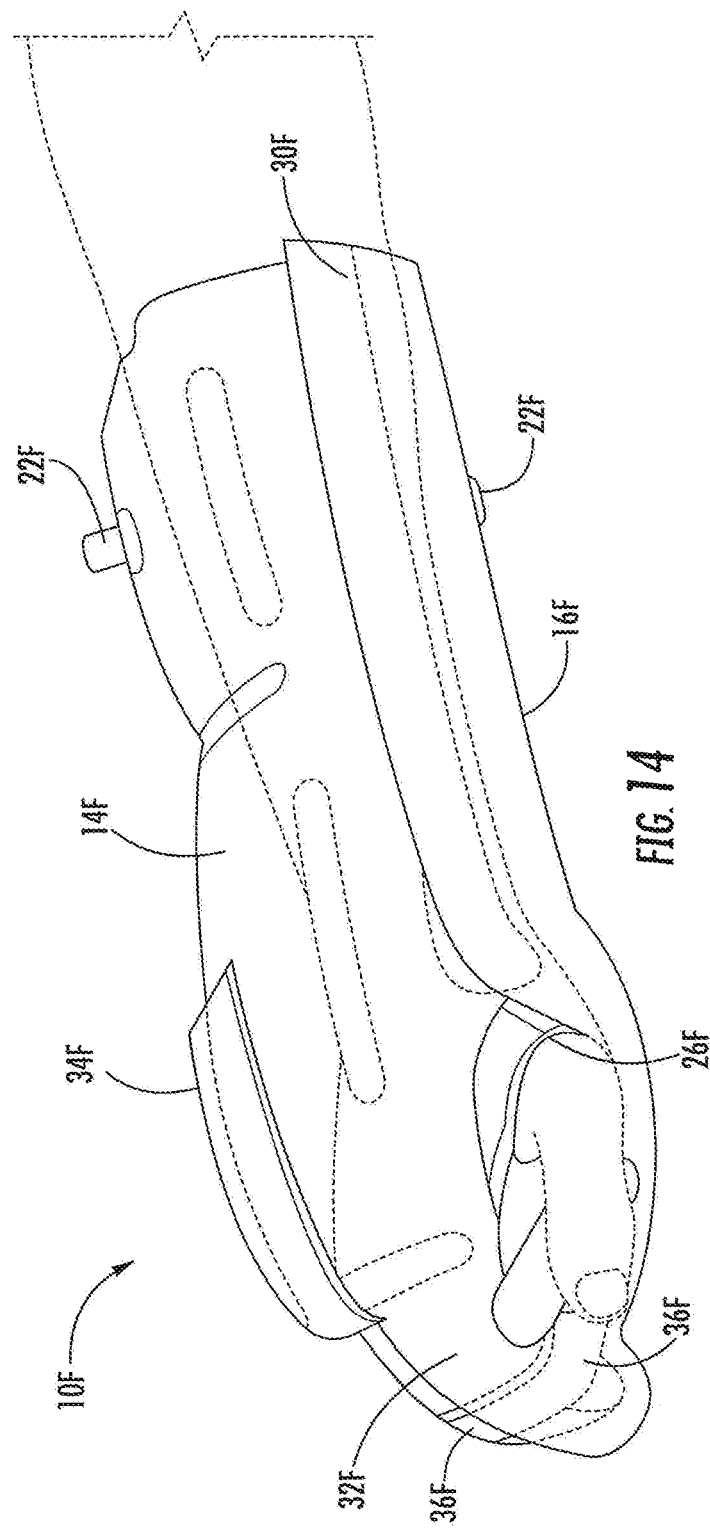
FIG. 14 is another perspective side view of the inflatable splint of FIG. 13 applied to a hand and a forearm.

Referring to FIG. 14, the chamber 32F of the splint 10F is inflated to keep the corresponding fingers (e.g., index finger and middle finger) in a desired position (e.g., half curled position), whereas the chamber 34F is deflated and strapped backward to give certain freedom to the corresponding fingers (e.g., ring finger and little finger) and keep them outside the splint 10F. One or more straps 36F can also be used to keep certain fingers in a bend position.

Figure 15:
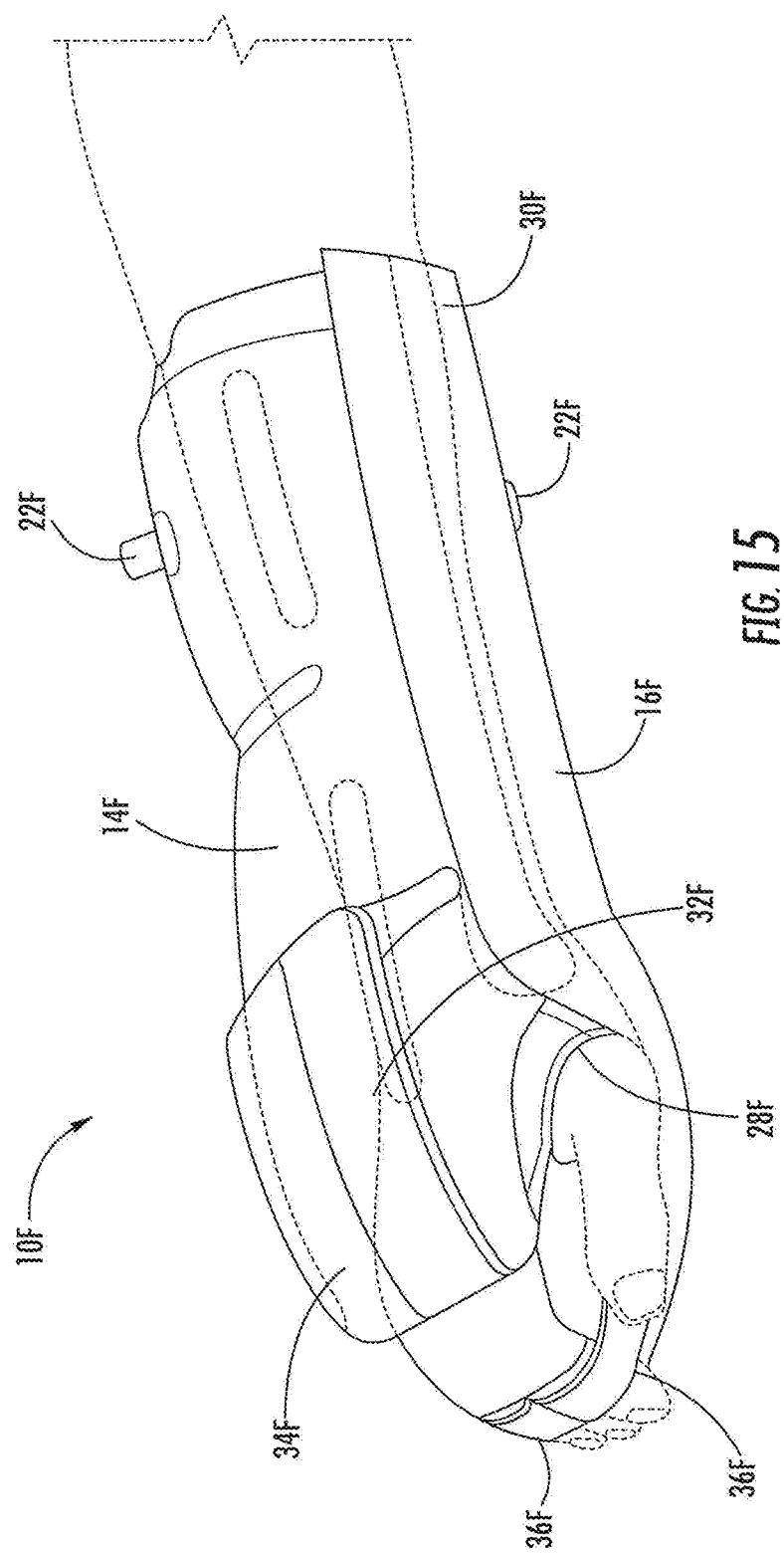
FIG. 15 is another perspective side view of the inflatable splint of FIG. 13 applied to a hand and a forearm, according to another embodiment of the present invention.

Referring to FIG. 15, both chamber 32F and 34F of the splint 10F are deflated and strapped backward to keep four fingers outside the splint 10F. One or more finger straps 36F are used to hold specific fingers in a desired position (e.g., bend position). In the depicted embodiment, one finger strap is used to hold the index finger and middle finger in a bent position, and another finger strap is used to hold the ring finger and little finger in a bent position. Alternatively, the four fingers can be left unstrapped for range of motion activities and functional activities, while still protecting the injured body part (e.g., wrist).

Figure 16:
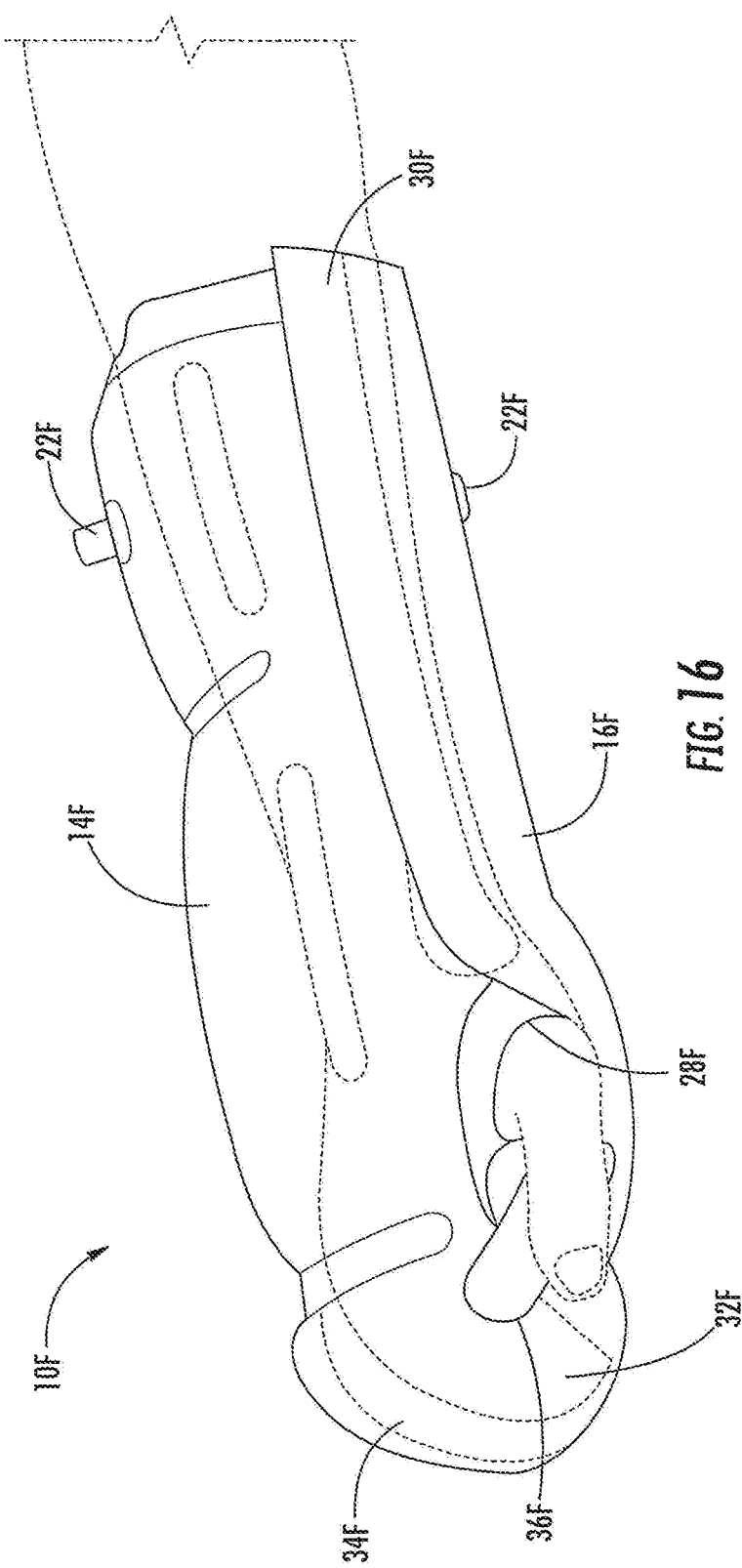
FIG. 16 is a perspective side view of the inflatable splint of FIG. 13 applied to a hand and a forearm, according to another embodiment of the present invention.

Referring to FIG. 16, both the chambers 32F and 34F of the splint 10F are inflated to keep the four fingers in a desired position (e.g., a functional position). In this case, one or more straps 36F can be attached to exterior of the chambers 32F and 34F to keep the chamber in a desired position.

Figure 17:
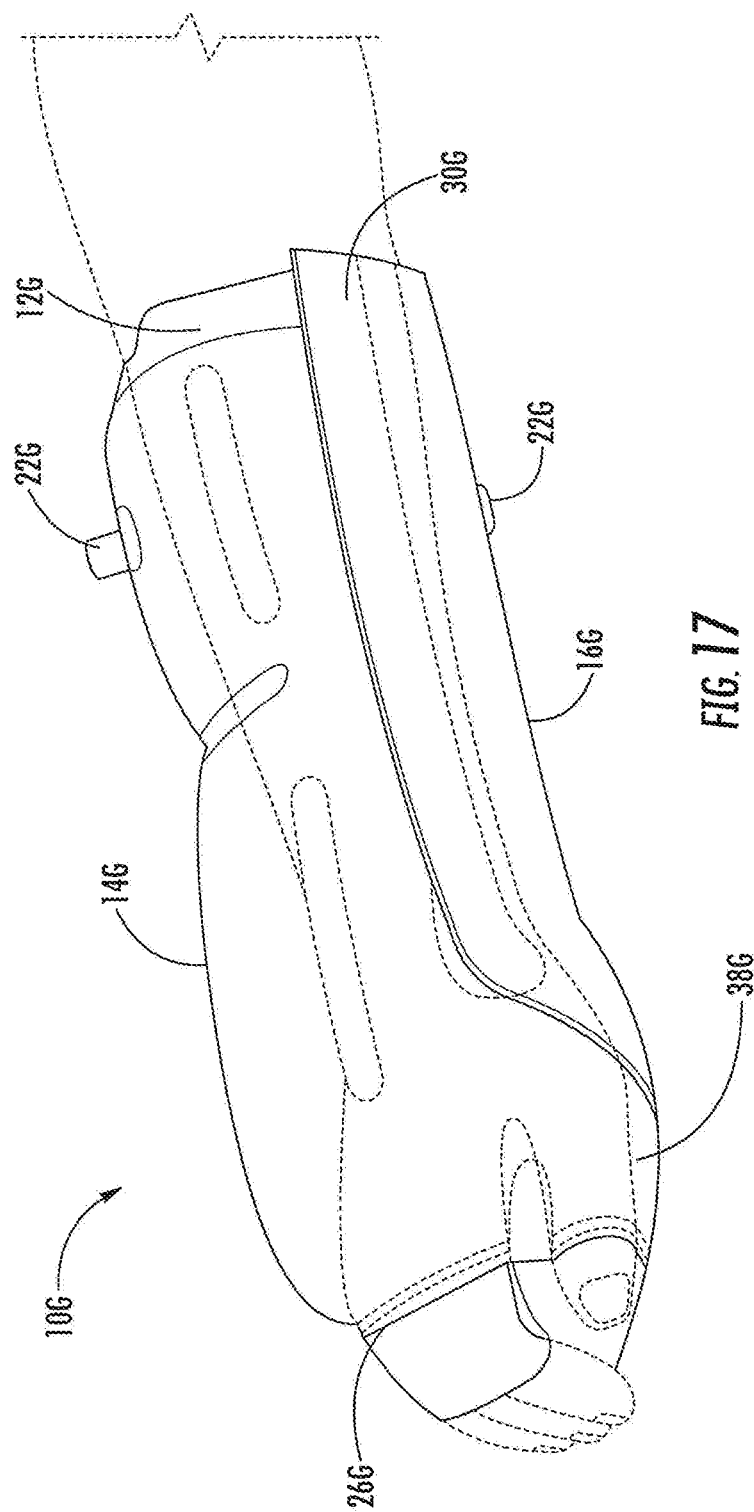
FIG. 17 is a perspective side view of an inflatable splint applied to a hand and a forearm, according to another embodiment of the present invention.

Referring to FIG. 17, according to another embodiment of the present invention, the splint 10G includes a chamber 14G surrounding a portion of the dorsal side of the hand and a portion of the arm, a chamber 16G surrounding a portion of the palmar side of the hand a portion of the arm, and a chamber 38G surrounding the thumb in the splint 10G. The inflated thumb chamber 38G can position the thumb in a desired position.

Figure 18:
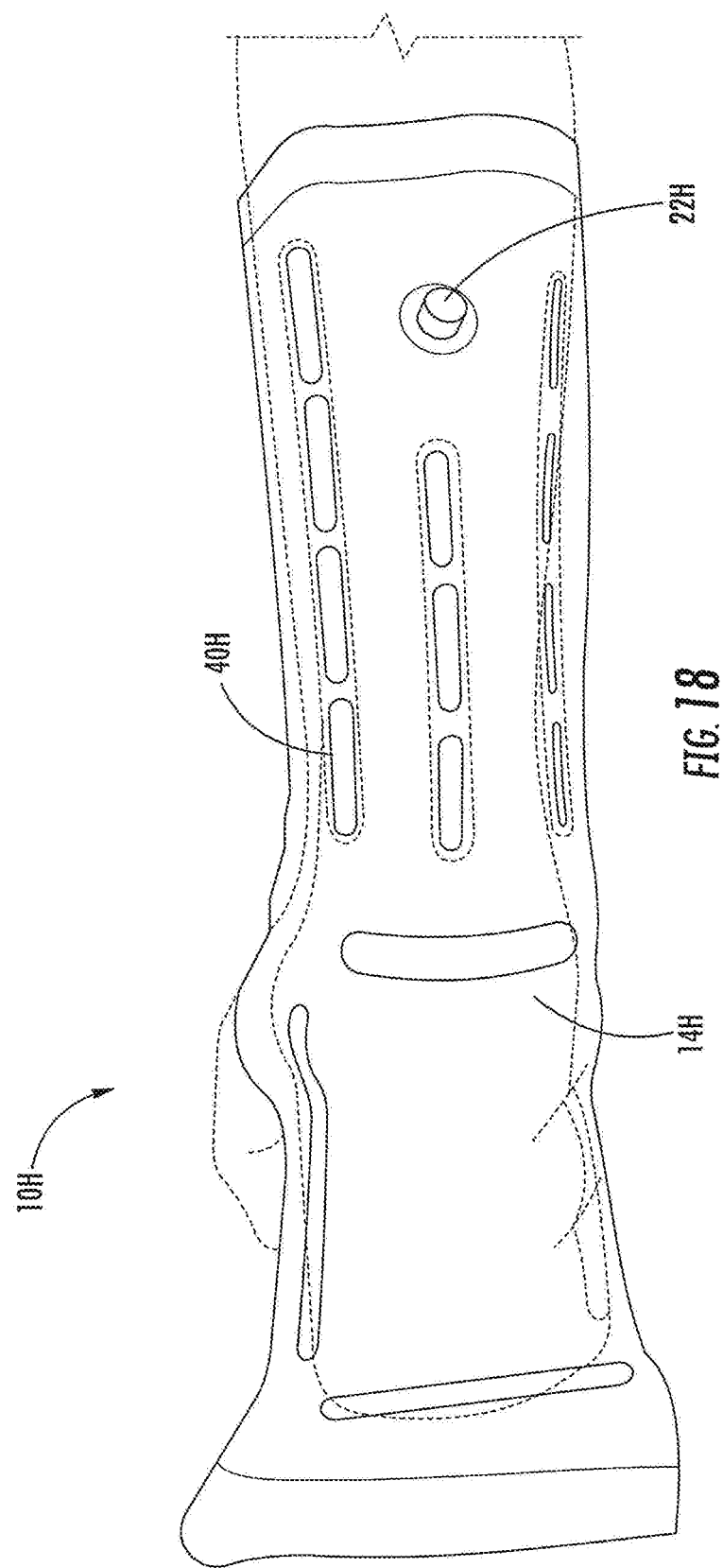
FIG. 18 is a perspective top view of an inflatable splint applied to a hand and a forearm, according to another embodiment of the present invention.

Referring to FIG. 18, according to another embodiment of the present invention, the splint 10H further includes a plurality of vent holes 40H in the sleeve 12H to allow airflow.

Figure 19:
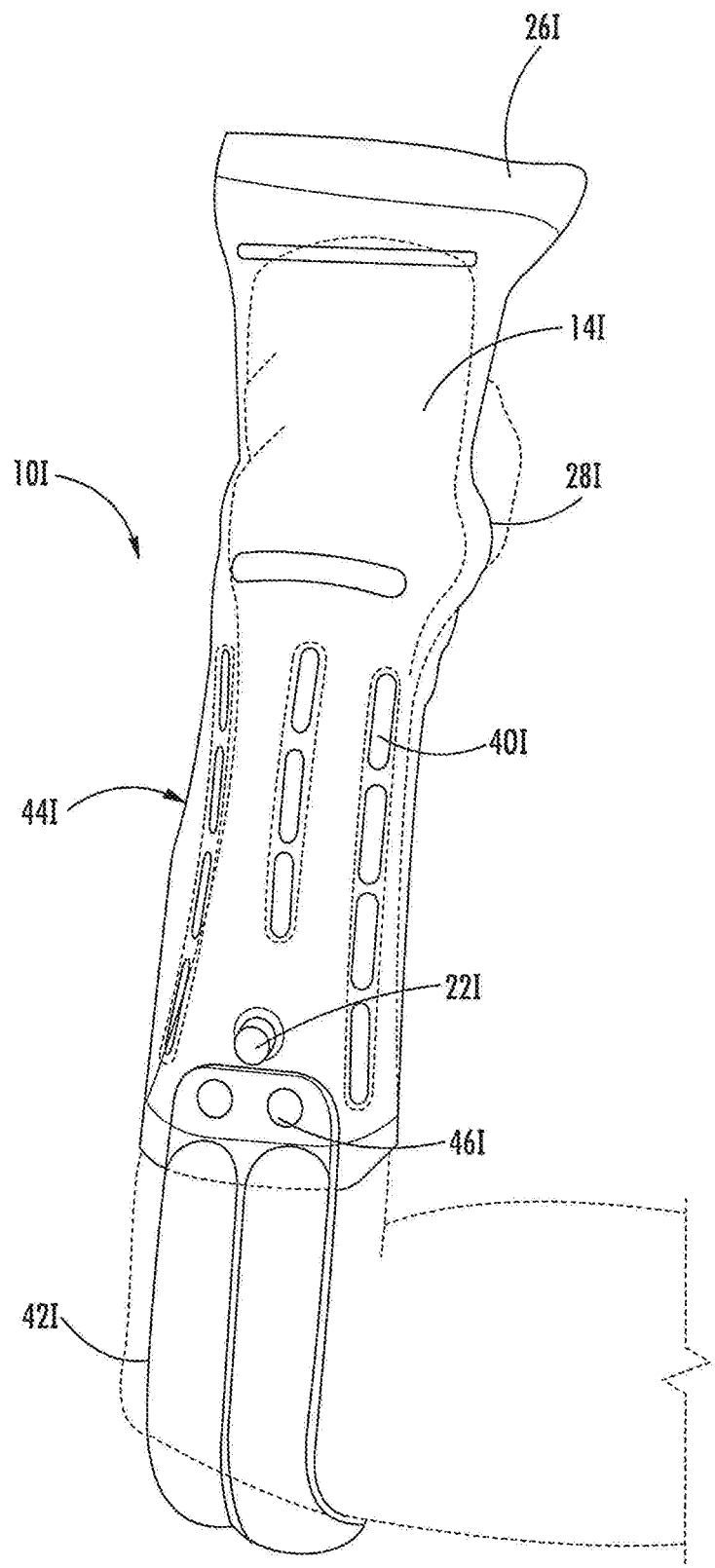
FIG. 19 is a perspective top view of an inflatable splint applied to a hand and a forearm, according to another embodiment of the present invention.

Referring to FIG. 19, the splint 10I further includes an elbow portion 42I releasably attached to a forearm portion 44I. For example, the elbow portion 42I can be connected to the forearm portion 44I via snap buttons 46I or other suitable means. The elbow portion 42I can hold a patient's elbow and forearm at relative orientation.

Figure 20:
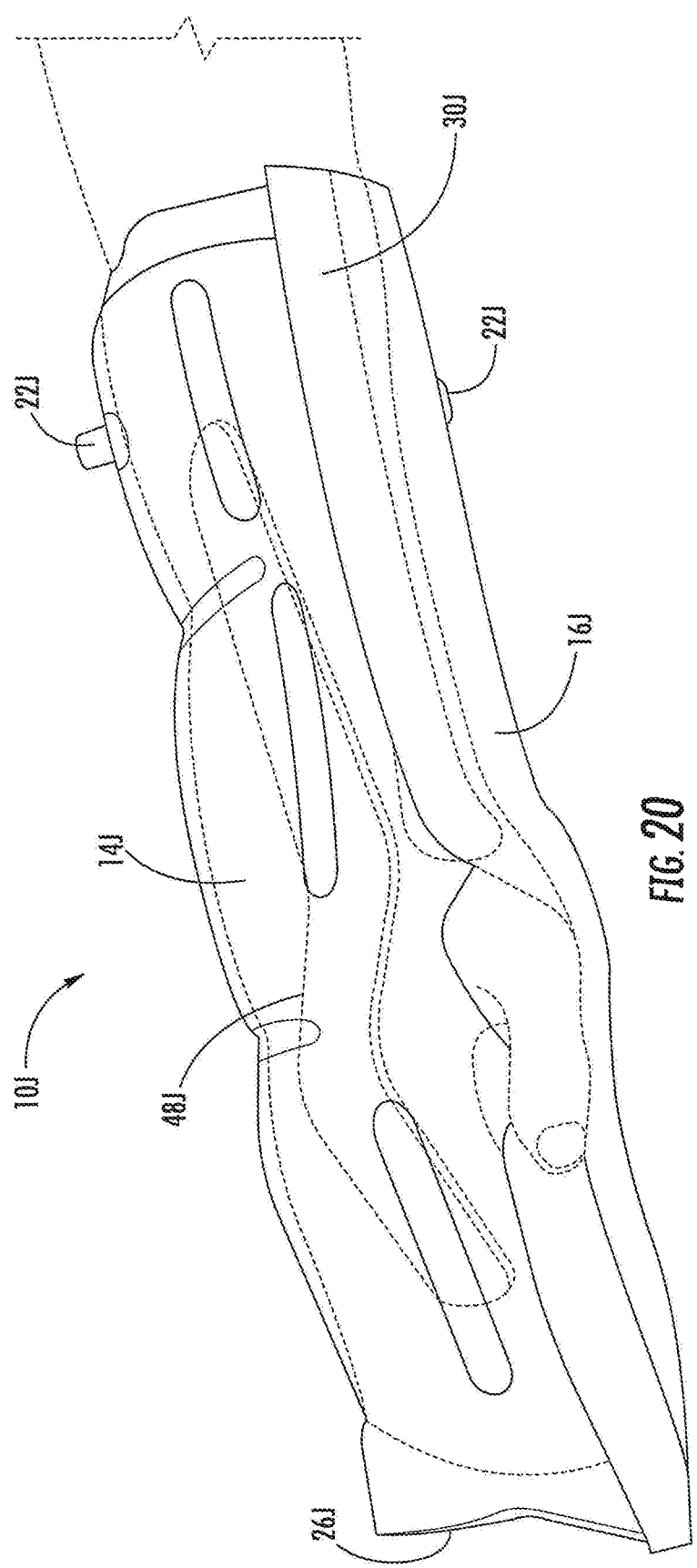
FIG. 20 is a perspective side view of an inflatable splint applied to a hand and a forearm, according to another embodiment of the present invention.

Referring to FIG. 20, according to another embodiment of the present invention, the splint 10J can include a rigid frame 48J covered by the sleeve 12J. The rigid frame 48J is used to hold a hand in a specific position. In the depicted embodiment, the rigid frame 48J is positioned on the dorsal side of the hand. One or more rigid frames can also be positioned on the palmer side of the hand or other appropriate position relative to a suitable body part.

The sleeve 12 can be made of a plastic material treated with an anti bacterial agent. The sleeve material is relatively soft and preferably somewhat elastic so that it can fit well around regions in the vicinity of a limb and/or joint.

The air chambers can be constructed of any material which lends itself to inflation by air or other compressed gases, such as rubber, rubberized fabric, plastic resins (e.g., polyvinyl chloride, polyethylene and polypropylene) and/or other elastomeric materials. The air chamber wall is of sufficient thickness and elasticity such that desired pressures and tensile forces can be achieved without excessive filling of the air bladder. The plurality of chambers can be made of two-ply material, one-ply material, or a combination thereof. The inner side of the chamber (the side that is closest to a patient's limb) can be made of a more pliable material than the outer side for a snug fit to the contours of the patient's limb and comfortable and even pressure applied to the patient's limb. The outer side of the air chamber (the side that is farthest away from the patient's limb) can employ a more rigid (e.g., raft-like) material than the inner side to apply a counterforce and control the overall dimension of the splint 10.

In use, a body part (e.g., a limb, a joint, a hand) is admitted into an open-ended sleeve, enabling the rapid and proper positioning, of a plurality of air chambers thereon prior to inflation. One or more of the plurality of air chambers can be inflated to maintain a body part in a desired position and/or orientation. Alternatively, a body part can be first positioned on an open sheet and the sheet can be wrapped into a tubular sleeve and sealed on the longitudinal edge of the sheet.

Figure 21:
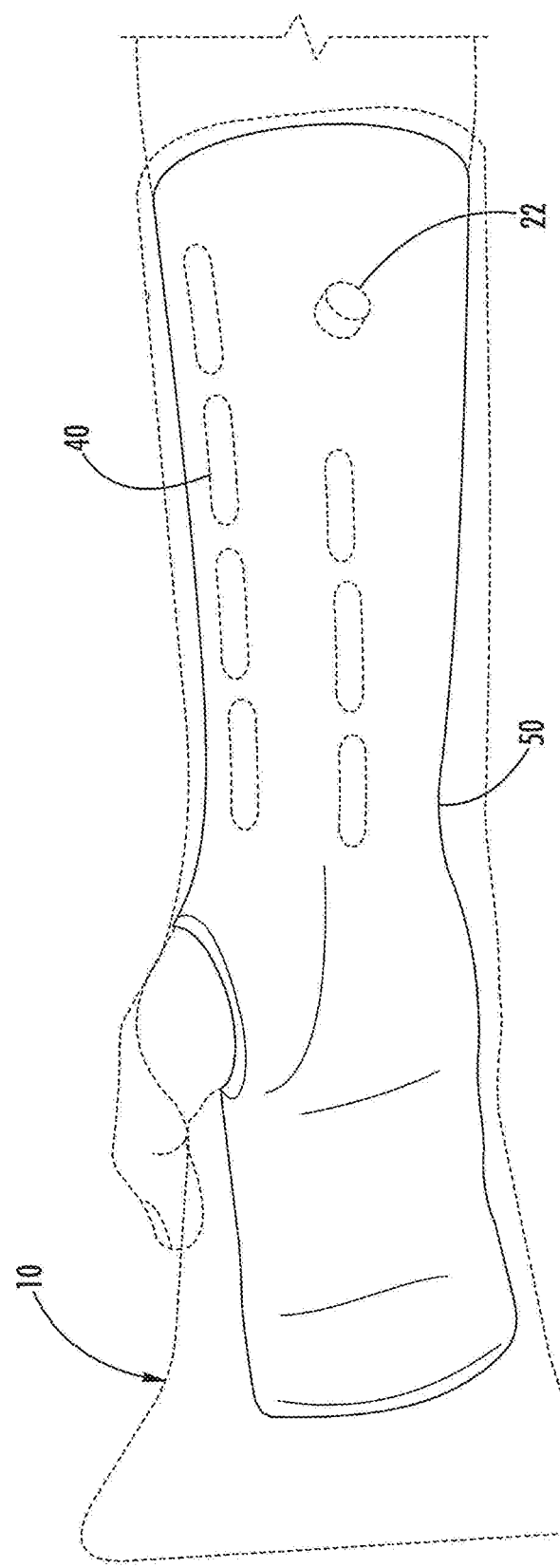
FIG. 21 is a perspective top view of an inflatable splint applied to a hand and a forearm, according to another embodiment of the present invention.

Referring to FIG. 21, according to one embodiment of the present invention, a body part can be covered with a fabric sock 50 before admitted to the sleeve to increase the comfort level of the patient. The fabric sock 50 can also be cleaned easily.

The disclosed splint can be secured into place via a variety of methods. For example, the air chambers of the splint are compressive enough to hold the splint 10 in place once inflated, as shown, for example, in FIGS. 1-8 and 11-20.

Figure 22:
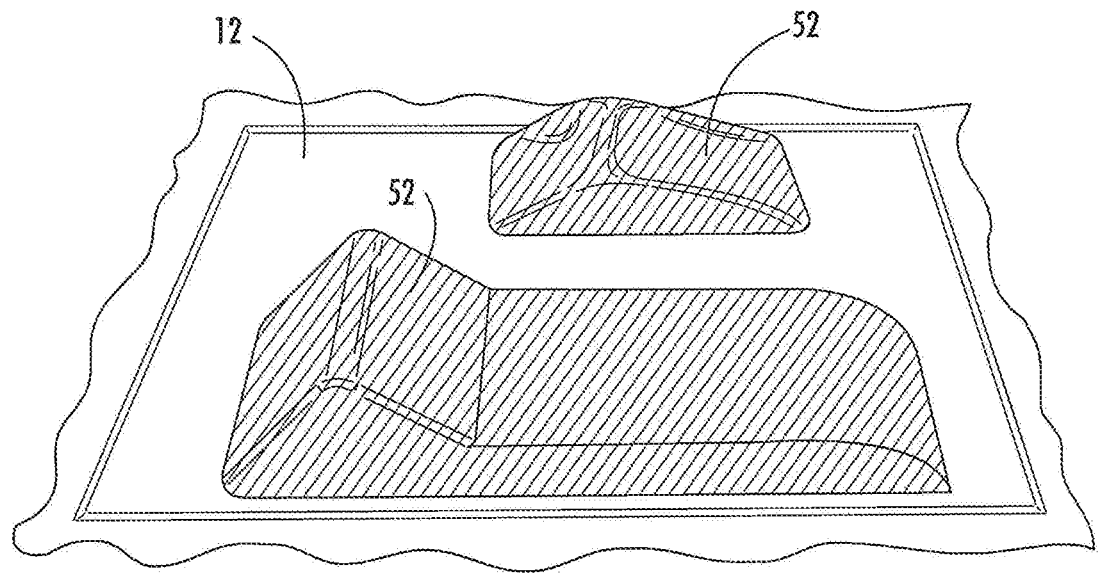
FIG. 22 is a perspective view of a plurality of molds positioning on a sheet for forming a plurality of air chambers, according to another embodiment of the present invention.
Figure 23:
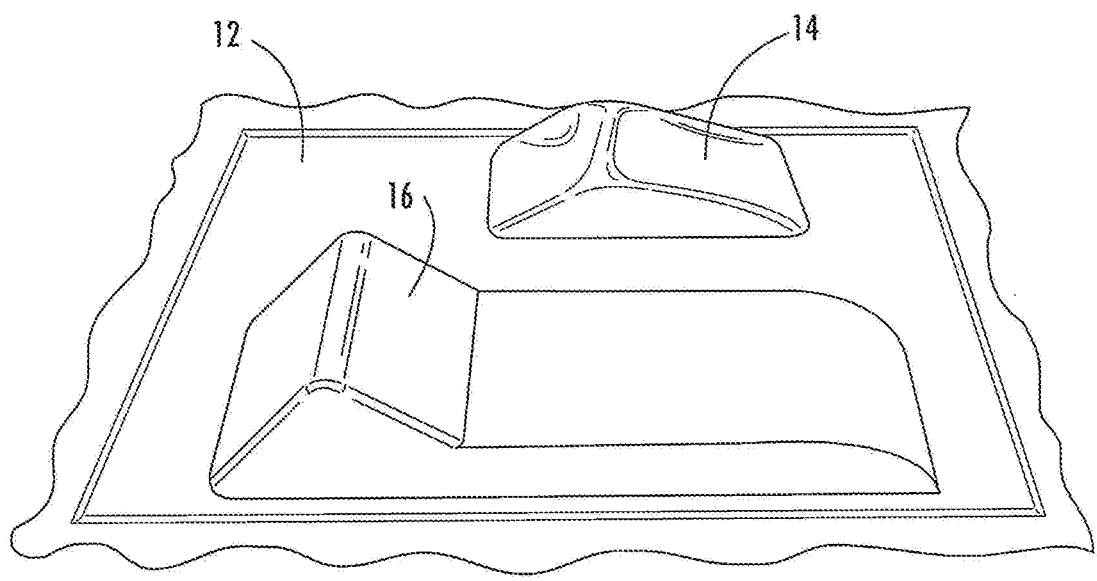
FIG. 23 is a perspective view of air chambers formed on the sheet of FIG. 22, according to another embodiment of the present invention.

Referring to FIGS. 22 and 23, the disclosed inflatable splint can be made by first determining locations of a plurality of air chambers on a sheet 12 and positioning respective molds 52 of predetermined dimension on the determined locations. A plurality of air chambers (e.g., chamber 14, chamber 16) are formed on the sheet according to the respective molds at the determined locations by, for example, RF bonding. One or more loops and fasteners (not shown) on at least one longitude edge of the sheet.

The splint of this invention can be quickly and properly positioned on a limb without causing any added discomfort or pain to the wearer. The highly flexible character of the splint enables it to be readily applied in a natural, conforming position even on such angular areas of the body as the juncture of the foot and ankle. The application of the splint does not require a person with previous experience with applying splints.

The splint of this invention allows an untrained team member to apply the splint to deliver an injured patient in comfort from the emergency care setting to a specialist, even if that visit is delayed for several days to one or more weeks. The splint can maintain the specific human body part in a specific predetermined position that preserves the long term functional position of the limb for the duration of the splinting process. As such, the splint can prevent further damage to the injured limb due to incorrect splint positioning and excessive tightness or pressure from the splint.

After deflation, the splint can be easily folded into a compact package for convenient carrying and storage such as a first aid kit. The uniquely simple construction of the splint, furthermore, enables it to be manufactured at minimal cost with conventional equipment from readily available materials. The inflatable splint is lightweight and therefore allows a user to move the body part inside the splint freely as a whole.

From the foregoing, it will be appreciated that an inflatable splint according to the present invention includes several easily constructed components which can be quickly adapted to conform a body part to an intended position or orientation. The inflatable splint can also be quickly and easily deflated and removed from the body part when it is not needed.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and the claims appended hereto.

What is claimed is:

1. An inflatable splint comprising:
   a sleeve shaped to conform to a specific human body part; and
   a plurality of inflatable chambers formed on the sleeve;
   wherein the sleeve, in cooperation with the plurality of inflatable chambers in inflated condition, is contoured and positioned to maintain the specific human body part in a desired position when the sleeve is positioned around at least part of the specific human body part;
   wherein the sleeve is shaped to conform to a portion of a hand and a lower arm; and
   wherein the plurality of inflatable chambers includes a first chamber surrounding at least a portion of a dorsal side of the hand and a dorsal side of the lower arm, a second chamber surrounding at least a portion of a palmar side of the hand and a palmar side of the lower arm, a third chamber configured to surround a dorsal side of an index finger and a middle finger, and a fourth chamber configured to surround a ring finger and a little finger, and wherein the third chamber and the fourth chamber are configured to be inflated separately.

2. The inflatable splint of claim 1, wherein the plurality of inflatable chambers are inflated by one or more valves attached on one or more of the plurality of inflatable chambers.

3. The inflatable splint of claim 2, wherein the one or more valves are inflatable by mouth.

4. The inflatable splint of claim 2, wherein the one or more valves are inflatable by a pump.

5. The inflatable splint of claim 1, wherein the plurality of inflatable chambers are conjoined.

6. The inflatable splint of claim 1, wherein the plurality of inflatable chambers are disjoined.

7. The inflatable splint of claim 1, wherein the plurality of inflatable chambers are selectively inflatable.

8. The inflatable splint of claim 1, wherein the sleeve is made of a plastic material.

9. The inflatable splint of claim 1, further comprising at least one strap for securing the splint to an intended position.

10. The inflatable splint of claim 1, further comprising a rigid frame immersed under the sleeve.

11. The inflatable splint of claim 10, wherein the rigid frame is configured to be positioned on the dorsal side of the hand.

12. The inflatable splint of claim 1, wherein the sleeve has one or more loop and fasteners attached along a longitude edge of the sleeve.

13. The inflatable splint of claim 1, wherein the sleeve includes a first portion shaped to conform to a first human body part, a second portion shaped to conform a second human body part, and wherein the first portion and the second portion are releasably connected to each other, and wherein respective one or more inflatable chambers are formed on the first portion and the second portion.

14. The inflatable splint of claim 1, further comprising one or more straps configured to hold one or more of four fingers in, a bend position.

15. The inflatable splint of claim 1, further comprising a fifth chamber surrounding a thumb on the hand.

16. The inflatable splint of claim 1, wherein the plurality of inflatable chambers are disjoined, and wherein the plurality of inflatable chambers are selectively inflatable.

17. The inflatable splint of claim 1, wherein the rigid frame is configured to be positioned on the dorsal side of the hand, and wherein the sleeve has one or more loop and fasteners attached along a longitude edge of the sleeve.

18. A method of using the inflatable splint of claim 1, comprising:
    admitting the specific human body part into the sleeve of the inflatable splint;
    positioning the sleeve around the specific human body part; and
    selectively inflating one or more of the plurality of inflatable chambers such that the sleeve in cooperation with the plurality of inflatable chambers in inflated condition are contoured and positioned to maintain the specific human body part in proper position.

19. The method of claim 18, wherein the step of positioning is performed to position the at least a portion of the dorsal side of the hand and the dorsal side of the lower arm within the first chamber of the plurality of inflatable chambers.

20. The method of claim 19, wherein the step of positioning is further performed to position the at least a portion of the palmar side of the hand and the palmar side of the lower arm within the second chamber of the plurality of inflatable chambers.

21. The method of claim 20, wherein the step of positioning is further performed to position the dorsal side of the index finger and the middle finger within the within the third chamber of the plurality of inflatable chambers.

22. The method of claim 21, wherein the step of positioning is further performed to position the ring finger and the little finger within the fourth chamber of the plurality of inflatable chambers.

23. The method of claim 22, wherein the inflatable splint further comprises a fifth chamber configured to surround a thumb on the hand, and wherein the step of positioning is further performed to position the thumb within the fifth chamber.

24. The method of claim 18, further comprising admitting the specific human body part into a fabric sock prior to admitting the body part into a sleeve.

25. A method of making an inflatable splint comprising:
    determining locations of a plurality of air chambers on a sheet;
    positioning respective molds of predetermined dimension on the determined locations;

forming the plurality of air chambers on the sheet according to the respective molds at the determined locations; and attaching one or more loops and fasteners on at least one longitude edge of the sheet.

26. The method of claim 25, further comprising forming one or more valves on one or more of the plurality of air chambers.

27. The method of claim 25, wherein the plurality of air chambers are formed on the sheet via radio frequency bonding.

28. The method of claim 25, wherein the one or more loops and fasteners are attached to the sheet via radio frequency bonding.

* * * * *